United States Patent [19]

Calcagno et al.

[11] 3,989,742

[45] *Nov. 2, 1976

[54] PROCESS FOR THE PRODUCTION OF VINYL ACETATE FROM ETHYLENE

[75] Inventors: Benedetto Calcagno, Milan; Claudio Divo, Saronno (Varese); Marcello Ghirga, Bresso (Milan), all of Italy

[73] Assignee: Societa' Italiana Resine S.I.R. S.p.A., Milan, Italy

[ * ] Notice: The portion of the term of this patent subsequent to Mar. 23, 1993, has been disclaimed.

[22] Filed: Oct. 1, 1969

[21] Appl. No.: 862,913

[30] Foreign Application Priority Data

Oct. 12, 1968   Italy.................................. 22412/68

[52] U.S. Cl............................. 260/497 A; 204/123; 204/149; 204/248
[51] Int. Cl.².......................................... C07C 67/05
[58] Field of Search .......... 260/497 A; 204/10, 109, 204/111

[56] References Cited
UNITED STATES PATENTS

| | | | |
|---|---|---|---|
| 1,982,160 | 11/1934 | Guinot............................ | 260/531 R |
| 3,346,624 | 10/1967 | Schaeffer et al................. | 260/497 A |
| 3,420,873 | 1/1969 | Olivier............................ | 260/497 A |
| 3,427,237 | 2/1969 | Morris............................ | 204/10 X |
| 3,459,644 | 8/1969 | MacClean et al............ | 260/604 R X |
| 3,461,157 | 8/1969 | Olivier et al.................... | 260/497 A |
| 3,492,340 | 1/1970 | Aguilo et al..................... | 260/497 A |
| 3,534,087 | 10/1970 | Leftin et al................. | 260/497 A X |

FOREIGN PATENTS OR APPLICATIONS

| | | | |
|---|---|---|---|
| 4,011,367 | 6/1965 | Japan.............................. | 260/497 A |
| 1,088,203 | 10/1967 | United Kingdom............. | 260/497 A |

OTHER PUBLICATIONS

Luder et al. *General Chemistry* 3rd Ed. Saunders (1965) pp. 192–193.
Perry, *Chemical Engr's Handbook* 4th Ed., McGraw Hill (1963) 19-22, 19-23.
Luder, *General Chemistry* (1965) pp. 238-251.

Primary Examiner—Lorraine A. Weinberger
Assistant Examiner—Michael Shippen
Attorney, Agent, or Firm—Sughrue, Rothwell, Mion, Zinn and Macpeak

[57] ABSTRACT

The copper and palladium ethylene-oxidation catalyst used in the preparation of vinyl acetate is regenerated in a process including deposition of the metals from solution in a Daniell-type galvanic cell and subsequent reconversion to the halides.

6 Claims, No Drawings

PROCESS FOR THE PRODUCTION OF VINYL ACETATE FROM ETHYLENE

The present invention relates to a process for the production of vinyl acetate from ethylene.

As is well known, vinyl acetate can be produced by bringing ethlyene and oxygen into contact with a palladium salt in an environment containing acetic acid, in the presence of a copper salt and salt of acetic acid that is ionised under the conditions of reaction.

It is also known that as the reaction of converting ethylene into vinyl acetate proceeds, a diminution in the activity of the catalyst is observed.

This phenomenon, which becomes more and more evident as time passes, results in a steady reduction in the mean specific production of vinyl acetate, which falls to levels below what is commercially acceptable. This phenomenon of continually falling specific production also creates awkward problems in the running of the entire plant.

For good progress and satisfactory operation in the reaction whereby vinyl acetate is formed from ethylene, there is obviously a need for maintaining the activity of the catalytic substance at values which are sufficiently high and which remain as far as possible constant with time.

To that end, it has been customary hitherto for the catalytic substance, once its activity has been reduced, to be subjected to combustion after withdrawal from the reaction vessel and separation from the acetic acid solution. This results in a solid mass consisting for the most part of oxides and chlorides of the metals composing the catalytic mixture, along with smaller amounts of those metals in their elementary form.

This mass is then suitably treated with acetic acid and hydrochloric acid, so as to regenerate the catalytic mixture, which is then returned to the reaction vessel in which the vinyl acetate is being produced.

The process described above, however, has a number of drawbacks, because of the complexity of the equipment used, the marked corrosive action due to the particular nature of the substance treated and to the high temperatures used, and the inevitable losses of catalyst arising, for example, from the volatility of the copper salts in the conditions of regeneration and from the carrying away of material in the combustion gases.

It has now been discovered that the drawbacks associated with the techniques known hitherto for the production of vinyl acetate by the catalytic oxidation of ethylene in the presence of acetic acid can be avoided or reduced if the catalytic mixture, when its activity is reduced, is removed from the reaction vessel in which the vinyl acetate is being produced and — containing as it does ions of copper, palladium, alkali or alkaline earth metals and chlorine or other halogen in acetic acid solution — is subjected to electrode position for separation of the palladium and copper in metallic form, the separation being followed by conversion of the metals back into the corresponding halides, which are fed back to the reaction vessel in which the vinyl acetate is being produced. More particularly, the catalytic mixture of reduced activity is withdrawn from the said vessel continuously or at prescribed intervals and transferred to a galvanic cell of the Daniell type.

The invention is hereafter described in terms of the use of alkali metals and chlorides in the catalytic mixture.

The cell preferably comprises a container divided, by a porous baffle or an ion exchange membrane, into two compartments, into which two electrodes dip. The catalytic mixture to be regenerated is run into one compartment, with one electrode, preferably of graphite or copper, immersed in it.

The other compartment contains a slightly acidic aqueous solution, in which is immersed an electrode consisting of an element that has an electro-chemical potential algebraically lower than those of copper and palladium.

When the two electrodes are joined externally by a suitable conductor, an electric current flows in that conductor, attended consequently by substantially quantitative deposition of copper and palladium on the electrode immersed in the catalytic mixture that is to be regenerated, with simultaneous oxidation of the element of algebraically lower potential.

(Herein, the European convention concerning electro-chemical potentials, according to which one system oxides all other systems having algebraically lower electro-chemcal potentials, is adopted.)

In a recommended practical application of the present invention, a copper or graphite plate immersed in the catalytic mixture to be regenerated is connected to a plate of metallic iron immersed in a dilute aqueous solution of hydrochloric acid.

This procedure is carried out with the catalytic mixture at a temperature between the limits of solidification and boiling of that mixture, and most conveniently maintained at between 40° C. and 85° C. though satisfactory results can be obtained outside those limits.

The solution from which the copper and palladium have been separated can be fed into a column of ion exchange resin of strong acid type in the acid form, in which, apart from possible traces of copper ions, the alkali held back. The effluent from the ion exchange column is sent for recovery — by distillation, for example — of the acetic acid. The ions held back by the column of resins, mainly alkali metal ions with small amounts of copper ions, are removed by one of the processes normally used for the purpose, such as by percolation of an acid solution through the column — preferably a dilute solution of hydrochloric acid.

The conversion of the metallic palladium and copper, recovered by easy removal from the electrode, to their corresponding chlorides, should preferably be carried out after the metals have been placed in suspension in a dilute aqueous solution of hydrochloric acid. In one of the recommended forms of the present invention, the metallic palladium and copper are placed in suspension in the effluent obtained by the treatment with dilute hydrochloric acid of the column of ion exchange resins and hence containing not only free hydrochloric acid, but also alkali metal chloride and possibly small amounts of copper chloride. Chlorine gas is bubbled into the resultant suspension in a suitable container maintained preferably at ambient temperature. This produces an aqueous solution of chlorides of the various metals, palladium, copper and alkali metal, from which the dissolved chlorine is removed, for example, by blowing in air.

Alternatively, conversion may be carried out by bubbling either air or oxygen into the aqueous hydrochloric suspension of metallic palladium and copper, preferably maintained at ambient temperature, in which condition dissolution appears to be more rapid.

The solution thus formed, containing substantially all the copper, palladium and alkali metal ions, removed from the reaction vessel for regeneration, is fed back into the vessel for the production of vinyl acetate along with acetic acid.

Normally, in the production of vinyl acetate from ethylene, ethylene and oxygen or an oxygen-containing gas are fed separately or mixed, with an ethylene/oxygen molar ratio of between 10:1 and 25:1 and preferably between 14:1 and 22:1, preferably at a pressure of between 20 and 50 atm., into a reaction vessel kept at a temperature of between 80° C. and 160° C. and preferably between 100° C. and 140° C. containing from 0.5 to 5 gramme-ions/liter of an alkali metal, 0.01 to 0.5 gramme-ion/liter of copper, 0.0002 to 0.02 gramme-ion/liter of palladium and 0.1 to 1 gramme-ion/liter of chlorine in acetic acid solution.

When the catalytic mixture is regenerated by the process here proposed and the foregoing operating procedure is adhered to, the yield of vinyl acetate is high and to all intents and purposes constant with time.

EXAMPLE 1

In a reaction vessel containing a catalytic mixture consisting of 474 g. of copper ion, 6.7 g. of palladium ion and 815 g. of lithium ion, dissolved in 70 litres of an acetic acid solution, a gaseous mixture consisting of 90% of ethylene, 5% of oxygen, 4% of carbon dioxide and 1% of nitrogen was re-cycled at the rate of 200 N. cu.m./hour.

The working pressure was maintained at 30 atm. and the temperature at 120° C.

Also fed continuously into the reaction vessel were a solution of acetic acid at the rate of about 25 liters an hour and hydrochloric acid sufficient to keep the chlorine ion concentration in the vessel at 0.25 gramme-ion/liter.

The mean specific production during the first 100 hours, expressed in mols of ethylene converted into acetate and acetaldehyde, was equivalent to 1.25 mols per liter of catalytic mixture per hour.

At that point, the whole of the catalytic solution, with its activity considerably reduced by then, was withdrawn from the vessel in which the vinyl acetate was being produced and run into one of the two compartments into which a container was divided by a porous baffle made of aluminium silicate, the pores in which had a mean diameter of one micron.

In this compartment, the temperature of which was maintained by an appropriate thermostatic system at 50° C., a plate of graphite of 0.1 sq.m surface area was immersed, this then being connected to a plate of metallic iron of 0.1 sq.m. surface area, immersed in a 1% aqueous solution of hydrochloric acid contained in the second compartment into which the container was divided by the porous baffle. When the two electrodes were joined together, the result was a system which acted as a galvanic cell, in which the half-cell consisting of the graphite plate and the catalytic mixture to be regenerated formed the positive pole, while the half-cell consisting of the iron plate and the 1% aqueous solution of hydrochloric acid formed the negative pole.

The connection between the two electrodes was maintained overnight. Palladium and copper were deposited substantially quantitatively on the graphite plate in the form of a thin deposit of low adhesion, which was easily removed.

The aqueous acid solution form which the palladium and copper had been separated was then discharged and passed into a column of DOWEX-50 ion exchange resin in the acid form. The liquid effluent minus cations and the water from the subsequent washing of the column were sent for distillation, to recover the acetic acid.

The column of ion exchange resins was then regenerated in acid form by washing with 10% aqueous hydrochloric acid, which produced an effluent consisting of a solution of lithium chloride, free hydrochloric acid and traces of copper chloride.

This solution and the deposit of metallic palladium and copper obtained on the electrode of the galvanic cell were placed in a suitable container maintained at ambient temperature, in which ha continuous stream of air ensured that the solid remained in suspension and was oxidised.

When no metal remained in suspension in the liquid, the solution, containing $PdCl_2$, $CuCl_2$ and $LiCl$, in a quantity substantially identical to that of the initial fresh catalytic solution, was fed, together with acetic acid (some of it that recovered), to the reaction vessel in which the vinyl acetate was being produced, where, in the same conditions as initially, it gave a mean specific production, expressed in mols of ethylene converted into vinyl acetate and acetaldehyde, equivalent to 1.2 mols per liter of catalytic mixture per hour.

We claim:

1. In a process for the production of vinyl acetate where ethylene and oxygen or an oxygen containing gas are fed into a catalytic mixture consisting essentially of the halogenides of palladium and copper, and an acetate selected from the group consisting of alkali metal and alkaline earth metal acetates in acetic acid, under conditions of high temperature and pressure, wherein the catalytic activity of said catalytic mixture becomes reduced during the progress of the reaction the improvement which comprises:

a. removing the catalytic mixture from the reaction vessel in which the vinyl acetate is being produced;
   b. recovering said copper and palladium in their elemental form by deposition in a Daniell-type galvanic cell, which consists of two compartments separated by a member selected from the group consisting of a porous baffle and an ion exchange membrane, one compartment containing the catlytic mixture and a first electrode upon which the copper and palladium are deposited, and the other compartment containing an aqueous acid electrolyte and a further electrode, electrically connected to the first electrode, consisting of an element of electrochemical potential algaebraically lower than the electrochemical potentials of copper and palladium;
   c. converting the recovered metallic palladium and copper to their corresponding chloride salts, by suspending the metallic palladium and copper in a dilute aqueous solution of hydrochloric acid and subsequently bubbling therethrough, a member selected from the group consisting of chlorine gas, air, and oxygen; and
   d. returning the palladium and copper salts thus formed to the reaction vessel in which the vinyl acetate is being produced, the temperature of the catalytic mixture during deposition of said metals being maintained between 40° C and 85° C.

2. The process of claim 1, wherein the electrode on which the copper and palladium are deposited is a member selected from the group consisting of graphite and copper.

3. The process of claim 1, wherein the element of lower potential is iron.

4. The process of claim 1, wherein the solution from which the copper and palladium have been separated is passed through a column of an ion exchange resin of the strong acid type, in which the alkali or alkaline earth metal ions are retained, the effluent thus being permitted to recover the acetic acid.

5. The process of claim 1, wherein the vinyl acetate is produced by feeding ethylene and a member selected from the group consisting of oxygen and an oxygen-containing gas, separately or mixed, with an ethylene/oxygen molar ratio of from 10:1 to 25:1, into a reaction vessel maintained at a temperature between 80° C and 160° C, further containing therein, 0.5 to 5.0 gram-ions per liter of alkali metal, 0.0002 to 0.02 gram-ion per liter of palladium, 0.1 to 0.5 gram-ion per liter of copper, and 0.1 to 1.0 gram-ions per liter of chlorine in a acetic acid solution.

6. The process of claim 5, wherein the ratio of said ethylene to oxygen ranges from 14:1 to 22:1, the temperature ranging from 100° C to 140° C, and the pressure ranging from 20 to 50 atmospheres.

* * * * *